United States Patent [19]

Patchel et al.

[11] Patent Number: 5,358,469

[45] Date of Patent: * Oct. 25, 1994

[54] DYNAMIC SPLINT

[75] Inventors: Kenneth A. Patchel, Kennett Square, Pa.; Andrew L. Mitchell, Wilmington, Del.

[73] Assignee: Ultraflex Systems, Inc., Malvern, Pa.

[*] Notice: The portion of the term of this patent subsequent to Aug. 6, 2008 has been disclaimed.

[21] Appl. No.: 740,387

[22] Filed: Aug. 5, 1991

Related U.S. Application Data

[63] Continuation-in-part of Ser. No. 477,460, Feb. 9, 1990, Pat. No. 5,036,837.

[51] Int. Cl.$^5$ .............................................. A61F 5/00
[52] U.S. Cl. ........................................ 602/5; 602/23; 602/26
[58] Field of Search .................... 602/5, 13, 23, 26, 27, 602/61, 62; 128/882

[56] References Cited

U.S. PATENT DOCUMENTS

| | | |
|---|---|---|
| 2,067,567 | 1/1937 | Gruca . |
| 2,832,334 | 4/1958 | Whitelaw . |
| 3,607,963 | 1/1973 | Keropian . |
| 3,826,251 | 7/1974 | Ross . |
| 4,340,041 | 7/1981 | Frank . |
| 4,397,308 | 8/1983 | Hepburn . |
| 4,485,808 | 12/1984 | Hepburn . |
| 4,489,718 | 12/1984 | Martin . |
| 4,508,111 | 4/1985 | Hepburn . |
| 4,538,600 | 9/1985 | Hepburn . |
| 4,614,181 | 9/1986 | Karlsson . |
| 4,624,247 | 11/1986 | Ford ................................ 602/26 |
| 4,657,000 | 4/1987 | Hepburn . |
| 4,697,583 | 10/1987 | Mason et al. . |
| 4,726,361 | 2/1988 | Farley . |
| 4,771,768 | 9/1988 | Crispin . |
| 4,817,588 | 4/1989 | Bledsoe ........................... 602/26 |
| 4,844,057 | 7/1989 | Hoy . |
| 4,846,842 | 7/1989 | Connolly ......................... 602/26 |
| 4,865,024 | 9/1989 | Hensley et al. . |
| 4,982,732 | 1/1991 | Morris . |
| 5,000,169 | 3/1991 | Swicegood et al. . |
| 5,002,044 | 3/1991 | Carter . |
| 5,013,037 | 5/1991 | Stermer . |
| 5,025,801 | 6/1991 | Callaway . |
| 5,092,321 | 3/1992 | Spademan . |
| 5,103,807 | 4/1992 | Makaran . |

OTHER PUBLICATIONS

International Search Report.

*Primary Examiner*—Michael A. Brown
*Attorney, Agent, or Firm*—Sixbey, Friedman, Leedom & Ferguson

[57] ABSTRACT

A dynamic splint provides a bias force with magnitude adjustable by a mechanism located at a pivotal joint. Specific embodiments include a dynamic ankle splint incorporating a correction cradle. The correction cradle applies a torsional force to the foot, thus permitting correction of inversion and eversion of the foot in conjunction with correction of dorsiflexion and plantar flexion. In another embodiment, a dynamic wrist splint attaches to the forearm and provides a novel palm interface which adjusts to apply force over a large area of the palm depending on the relative angular position of the hand. A flexion strap is provided at the back of the hand for applying flexion forces. Further aspects of the invention include visible display of the bias magnitude. The relative magnitude is indicated by numeric markings on a rotating member of the adjustment mechanism. The portion of the rotating member having the appropriate magnitude marking is visible through an aperture in the housing. Additionally, a pin lock mechanism is provided for locking the strut members to prevent relative movement thereof and to temporarily prevent the application of force by the bias unit during attachment and removal of the splint.

34 Claims, 10 Drawing Sheets

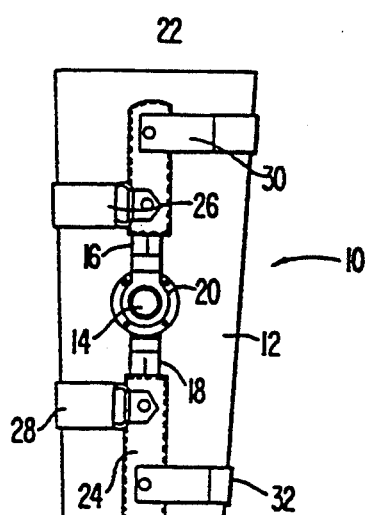
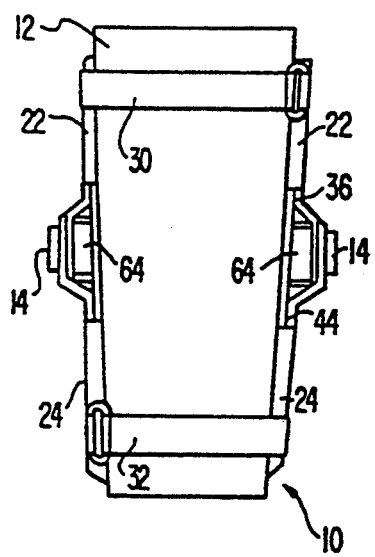
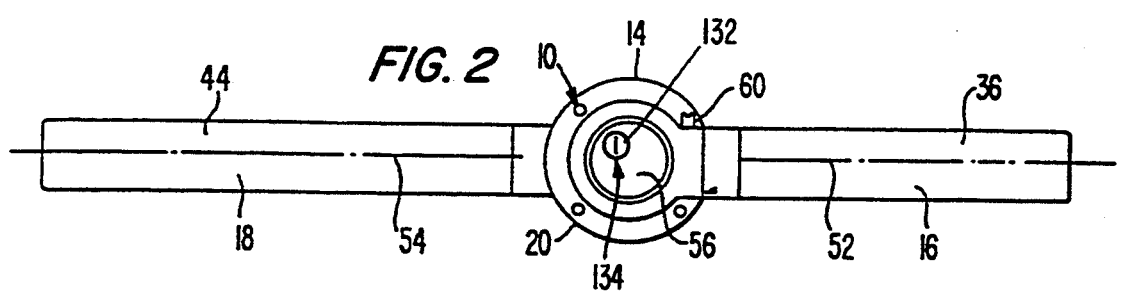
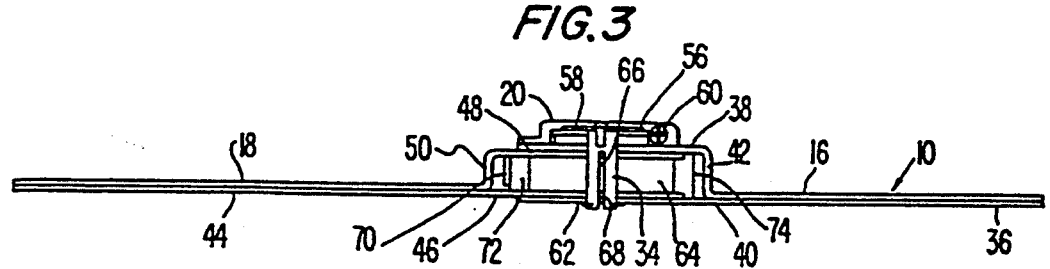

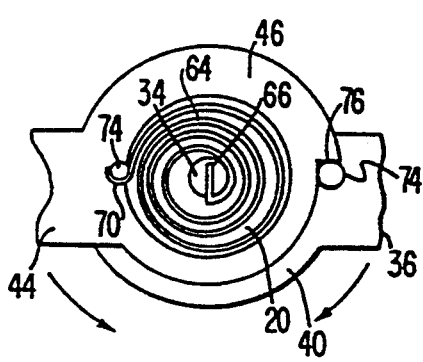
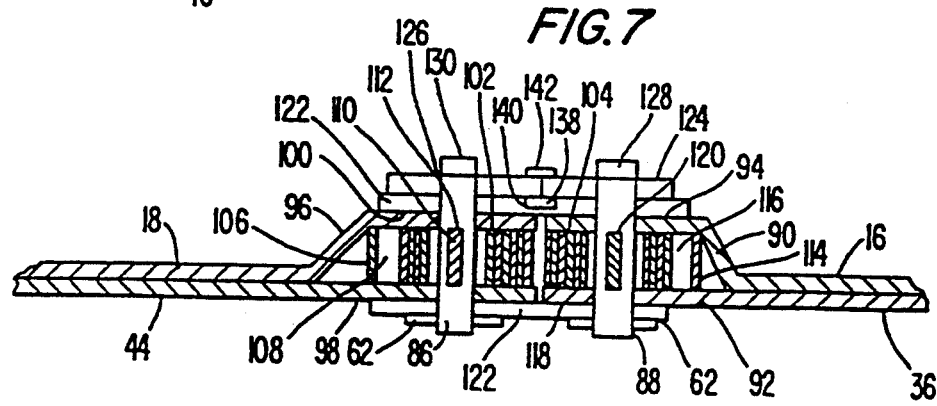

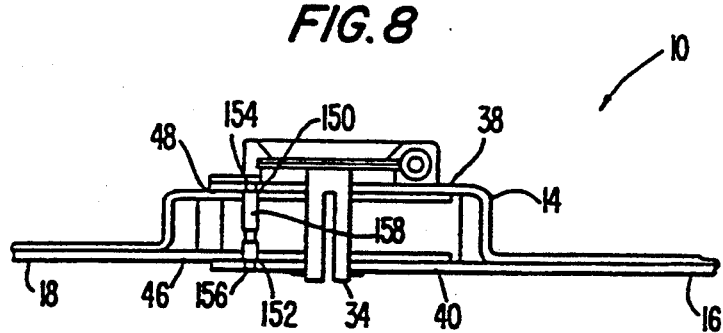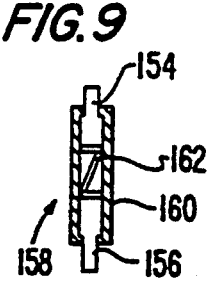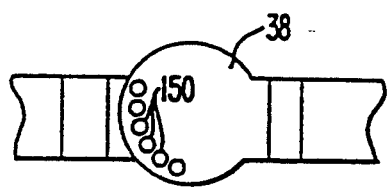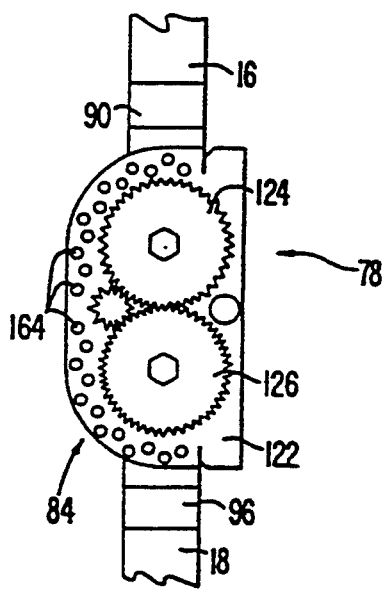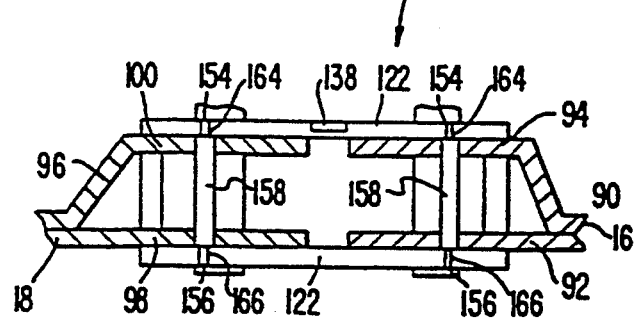

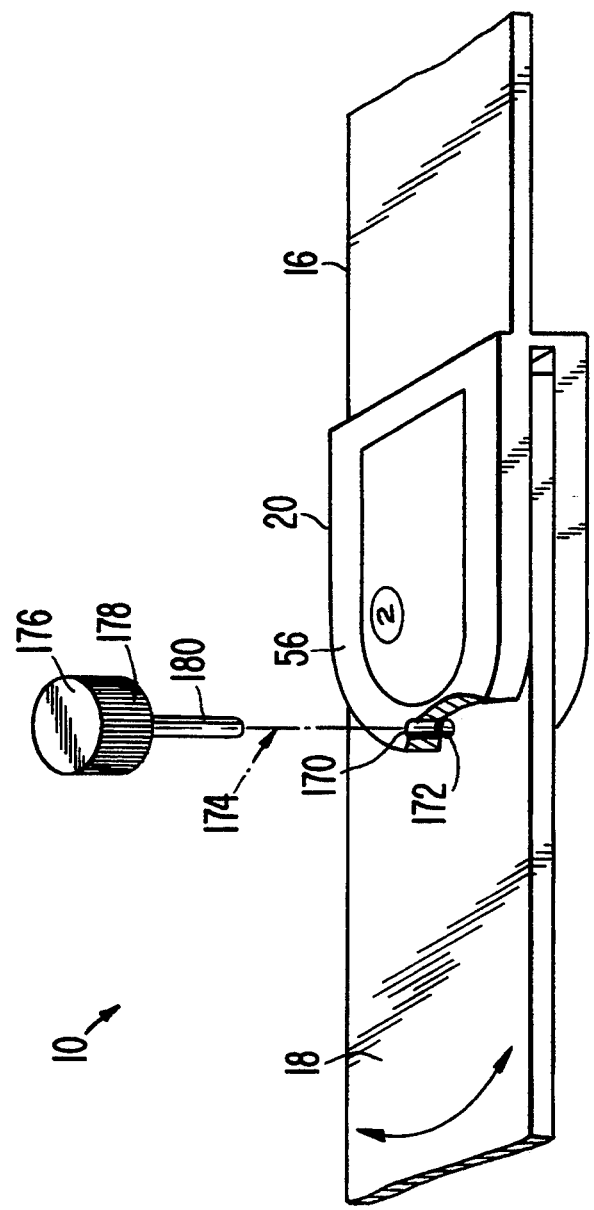

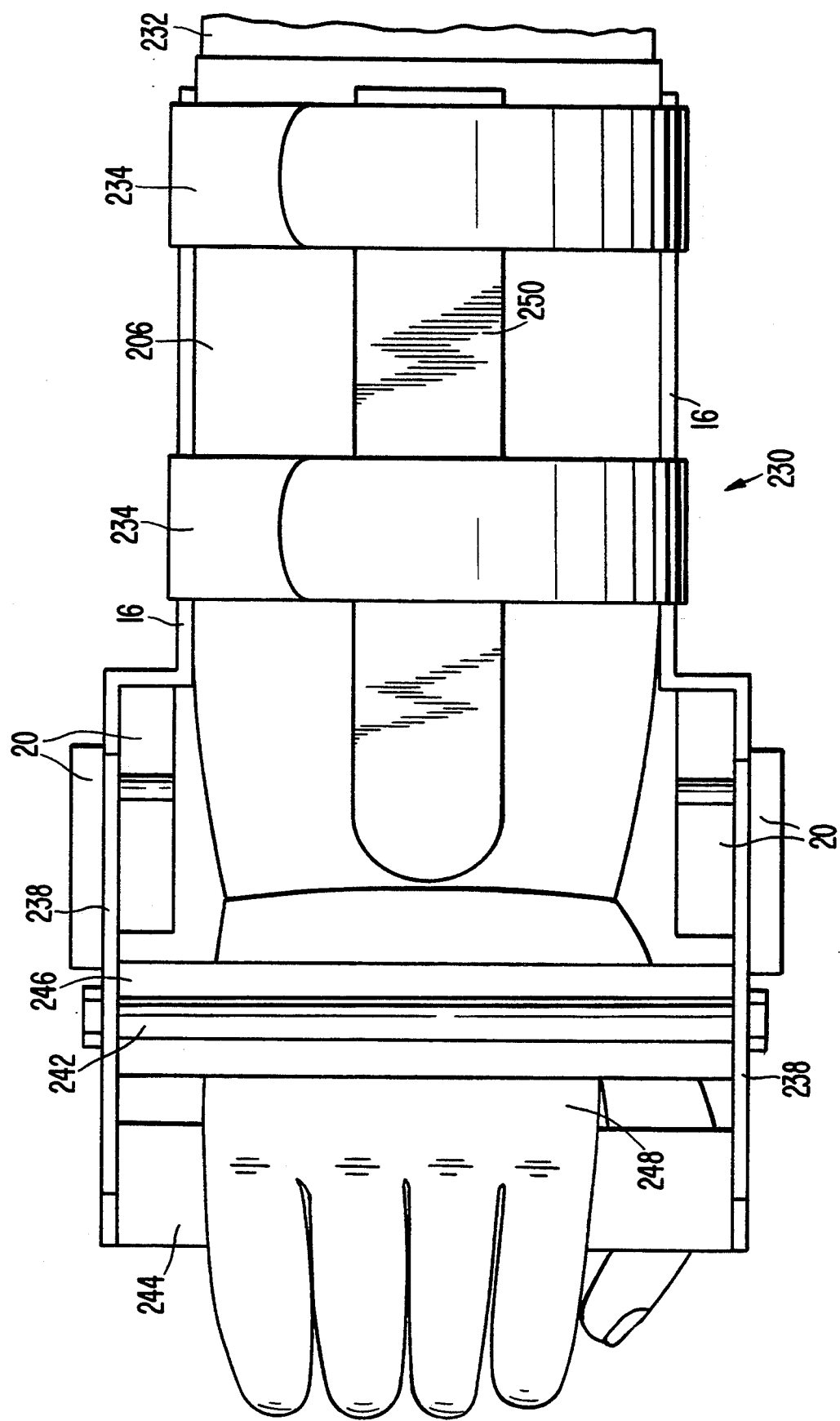

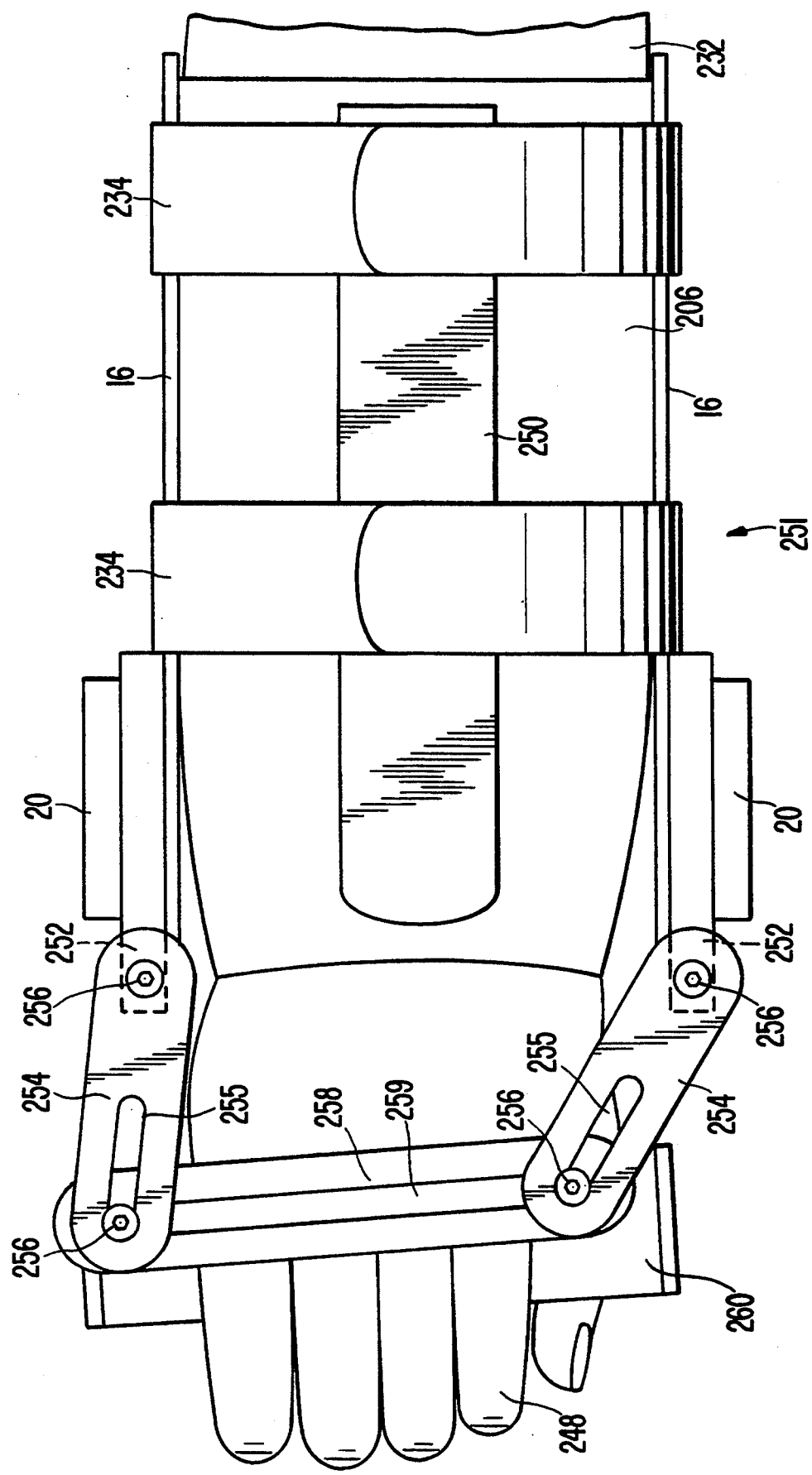

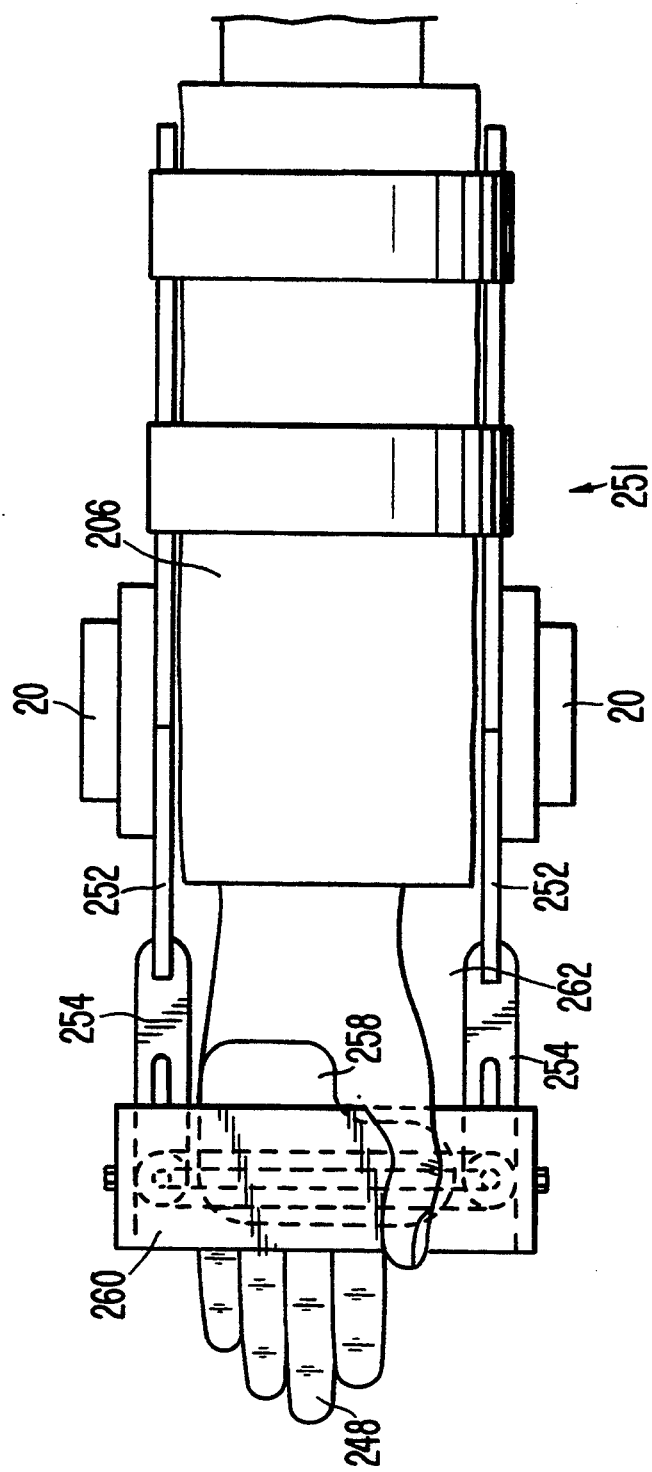

DYNAMIC SPLINT

RELATED APPLICATIONS

This application is a continuation-in-part of copending U.S. patent application Ser. No. 07/477,460, filed Feb. 9, 1990, now issued as U.S. Pat. No. 5,036,837.

FIELD OF THE INVENTION

The present invention relates to splint assemblies generally, and more particularly to a dynamic splint adapted to exert an adjustable force or tension at a body joint.

BACKGROUND OF THE INVENTION

In recent years, dramatic advances have been made in the development of lightweight, compact mechanisms for correcting common and debilitating injuries to body joints such as fingers, wrists, knees, elbows and the like. Perhaps the greatest advances have been made in the design of orthotic brace units which counteract instabilities in a joint by reinforcing the joint as a whole to prevent unwanted motion. Such orthotic devices are typically formed with a mechanical joint supported by a pair of bracing members. The mechanical joint is defined by a pair of side bars, each of which has a hinge-like pivoting joint in its middle with the top and bottom ends of the side bars being connected to bracing members which fit around a body portion above and below the joint to be supported. These devices operate generally by confining the movement of the joint as it bends so that unwanted motions are eliminated or at least minimized. The most commonly known orthoses are orthotic knee braces of the type commonly used by athletes who have suffered injuries to either the ligaments that interconnect the lower femur and upper tibia, or to the bones themselves, which result in knee instabilities.

Joint instability is not the only debilitating condition of a body joint which requires correction. The operation of a body joint may be impaired in a manner which inhibits the operation of the Joint in accomplishing extension or flexion. For example, a flexion contracture prevents full extension of the joint, while an extension contracture prevents the joint from being bent or flexed to the full extent. Obviously, the treatment of a flexion contracture or an extension contracture requires more than the mere support against instability provided by many conventional orthotic devices.

To treat flexion and extension contractures, spring-biased splint units have been developed to provide a force across a body joint. These splint devices provide tension which operates in opposition to a flexion or extension contracture and thereby not only provide support in instances where muscular weakness exists, but also enhance rehabilitation. One type of known adjustable spring-loaded splint includes a pair of lower struts and a pair of upper struts of tubular configuration which are pivotally interconnected. Spring biasing units mounted within the tubular struts are adapted to apply an adjustable force at the pivot point which tends to align the two pivoted struts. Such an adjustable splint mechanism is illustrated by U.S. Pat. Nos. 4,397,308; 4,485,808; 4,508,111; 4,538,600 and 4,657,000 to George R. Hepburn.

Although known adjustable splints operate effectively to apply tension across a joint, they are relatively heavy and bulky and consequently impede to some extent free activity at the affected joint. The heavy tubular strut assemblies used in prior art splints are generally not coextensive from the connecting pivot point, and thus may be brought into only parallel rather than axially aligned relationship. It is impossible to contour these heavy struts to conform to the limb of a user, and the degree of pivotal movement within which the applied force is linear is generally small. Such splints generally use straight line springing against a cam. The rotational force applied by the cam is extremely non-linear due to the changing moment arm on the cam surface. This variation prevents the application of a constant therapeutic force and requires constant adjustment to the spring force through the desired range of motion.

Finally, with known prior art adjustable splints, the bias adjustment mechanism for the splint is difficult to reach, and the degree of adjustment is often difficult to ascertain. Accurate adjustment of the bias for such prior art units with the splint in place is not easily accomplished, and the bias structure employed does not facilitate polycentric joint structures of the type better suited to the motion of certain joints, such as the knee.

SUMMARY OF THE INVENTION

It is a primary object of the present invention to provide a novel and improved dynamic extension or flexion splint for the treatment of joint contractures which is easily applied to a body member in the area of the joint to be treated and which is both compact and lightweight.

Another primary object of the present invention is to provide a mechanism for applying an adjustable force with near-constant linearity opposing movement of a body joint.

Another object of the present invention is to provide a novel and improved dynamic extension or flexion splint having opposed strut assemblies which incorporate flat strut members adapted to be contoured in place to conform to a body member. This permits customization of the splint for greater comfort.

A further object of the present invention is to provide a novel and improved dynamic extension and/or flexion splint having opposed strut assemblies which may be easily removed from a strut assembly support unit. Each strut assembly includes two elongated strut members which slide into pockets on either side of the joint to be treated.

Yet another object of the present invention is to provide a novel and improved dynamic extension and/or flexion splint which provides a full range of motion for a joint under treatment. The splint incorporates strut members which pivot at a mechanical joint through the maximum anatomical range plus 10° at each end. Tension is applied to the strut members by a torsion or power-spring type of biasing unit with near linear force characteristics mounted at the mechanical joint, and the spring tension is adjustable by means of a bias adjustment mechanism which is also located at the mechanical joint. Thus, the tension applying spring and the bias adjustment are both located entirely at the mechanical joint for the splint.

A further object of the present invention is to provide a novel and improved dynamic extension and/or flexion splint having a polycentric joint mechanism which is adapted to provide greater than the full anatomical range of motion. Elongated strut members are mounted on the joint for pivotal motion about two spaced parallel pivot axes. Each strut member is biased by a separate spring, and the bias of plural springs is simultaneously adjusted by a bias adjustment mechanism. An indicator at the mechanical joint provides an indication of the degree of bias which is set into the springs.

A still further object of the present invention is to provide a dynamic extension and/or flexion splint having an adjustable spring mechanism which is reversible to provide either flexion or extension resistance.

Another object of the present invention is to provide an adjustable-bias dynamic extension and/or flexion splint with a visible indicator showing the relative magnitude of the bias force applied.

A further object of the present invention is to provide an adjustable-bias dynamic extension and/or flexion splint wherein the bias force is produced by a mechanism in a housing located at the joint, and a visible indicator of the relative magnitude of the bias force is provided when different inscribed portions of a member rotating upon bias force adjustment become visible through an aperture as a result of the rotation.

It is also an object of the present invention to provide a dynamic extension and/or flexion splint, having portions attachable to a human body on each side of a body joint and applying a bias force to the joint, which also has a mechanism for selectively negating the bias force during attachment or removal of the splint.

Another object of the present invention to provide a dynamic extension and/or flexion splint, having portions attachable to a human body on each side of a body joint and applying a bias force of adjustable magnitude to the joint, which also has a mechanism for selectively negating the bias force during attachment or removal of the splint without changing the magnitude adjustment setting the bias force to be applied.

It is also an object of the present invention to provide a dynamic splint which is designed to be easily attached to a body joint in a flexible manner that compensates for deviations in the geometry of the joint and permits attachment of the splint even to damaged or swollen joints.

A further object of the present invention is to provide a dynamic ankle splint with a cradle for applying a torsional load to the ball of the foot to correct inversion and eversion of the ankle.

Yet another object of the present invention is to provide a dynamic wrist splint which is attached to the forearm, and applies a bias force to the hand through a novel palm interface.

It is also an object of the present invention to provide a dynamic wrist splint which distributes forces over a large area of the palm.

A further object of the present invention is to provide a dynamic wrist splint which adjusts over the wrist's arc of rotation to comfortably distribute forces over the palm.

These, and other objects of the present invention are accomplished by providing an adjustable splint having a pair of elongated strut assemblies which each incorporate a pivotal joint between the ends thereof. These strut assemblies are supported on opposite sides of a body joint by a strut support unit which is mountable on a body member and which locates the pivotal joint in alignment with a body joint. Each strut assembly includes a first elongated strut member and a second elongated strut member which extend from the pivotal joint. The elongated strut members of each strut assembly are flat units which may be contoured to match the contour of the body member upon which the splint is mounted. The pivotal joint operates to connect one end of the first and second strut members for pivotal movement about a pivot axis between a first extended position where the elongated strut members extend outwardly from opposite sides of the pivotal joint and a second closed position where the first and second strut members extend outwardly in close proximity from the same side of the pivotal joint. A bias unit is provided at the pivotal joint to oppose pivotal movement of the strut members in a first direction and to aid such pivotal movement in a second opposite direction. The magnitude of the bias is adjustable by a mechanism which is also located at the pivotal joint, while the range of motion provided by the joint can be altered by spring loaded pins which operate as stops for the strut members. The relative magnitude of bias provided is indicated in a preferred embodiment by numeric markings on a rotating member of the adjustment mechanism. The portion of the rotating member having the appropriate magnitude marking is visible through an aperture in the housing. A pin lock mechanism is provided for locking the strut members to prevent relative movement thereof and to temporarily prevent the application of force by the bias unit during attachment and removal of the splint.

Specific preferred embodiments of the invention include a dynamic ankle splint incorporating a correction cradle. The correction cradle applies a torsional force to the foot, thus permitting correction of inversion and eversion of the ankle in conjunction with correction of dorsiflexion and plantar flexion. A dynamic wrist splint attaches to the forearm and provides a novel palm interface which adjusts to apply force over a large area of the palm depending on the angular position of the hand. A flexion strap is provided at the back of the hand for applying flexion forces.

The dynamic splints disclosed permit maintenance of a defined tolerable force level with near constant linearity over a wide range of motion of a body joint. The dynamic splints are particularly useful for prophylactic maintenance of range-of-motion and mobility, particular in post-operative cases.

BRIEF DESCRIPTION OF THE DRAWINGS

FIG. 1 is a view in side elevation of the dynamic extension splint of the present invention;

FIG. 2 is a plan view of a strut assembly for the dynamic extension splint of FIG. 1;

FIG. 3 is a sectional view of the strut assembly of FIG. 2;

FIG. 4 is a view in front elevation of the strut assembly of FIG. 1;

FIG. 5 is a sectional view of a biasing spring assembly used in the strut assembly of FIG. 3;

FIG. 6 is a view in side elevation of a second embodiment of the dynamic extension splint of the present invention;

FIG. 7 is a sectional view of a strut assembly for the dynamic extension splint of FIG. 6;

FIG. 8 is a sectional view of the strut assembly of FIG. 2 showing a range of motion stop assembly;

FIG. 9 is a sectional view of a spring loaded pin used in the range of motion stop assembly of FIG. 8;

FIG. 10 is a partial plan view of the strut assembly of FIG. 8;

FIG. 11 is a partial plan view of a strut assembly for the dynamic extension splint of FIG. 6 showing a range of motion stop assembly;

FIG. 12 is a partial sectional view of the strut assembly of FIG. 11;

FIG. 13 is a side view of a locking pin according to the present invention, installed through the housing and into the strut assembly to prevent relative rotation of the struts;

FIG. 17 is a top view of the wrist brace of FIG. 16;

FIG. 18 is a top view of another embodiment of the wrist brace of the present invention, incorporating a modified palm interface design; and FIG. 19 is a bottom view of the wrist brace of FIG. 18 showing the palm interface thereof in greater detail.

DESCRIPTION OF THE PREFERRED EMBODIMENTS

Figure 14:
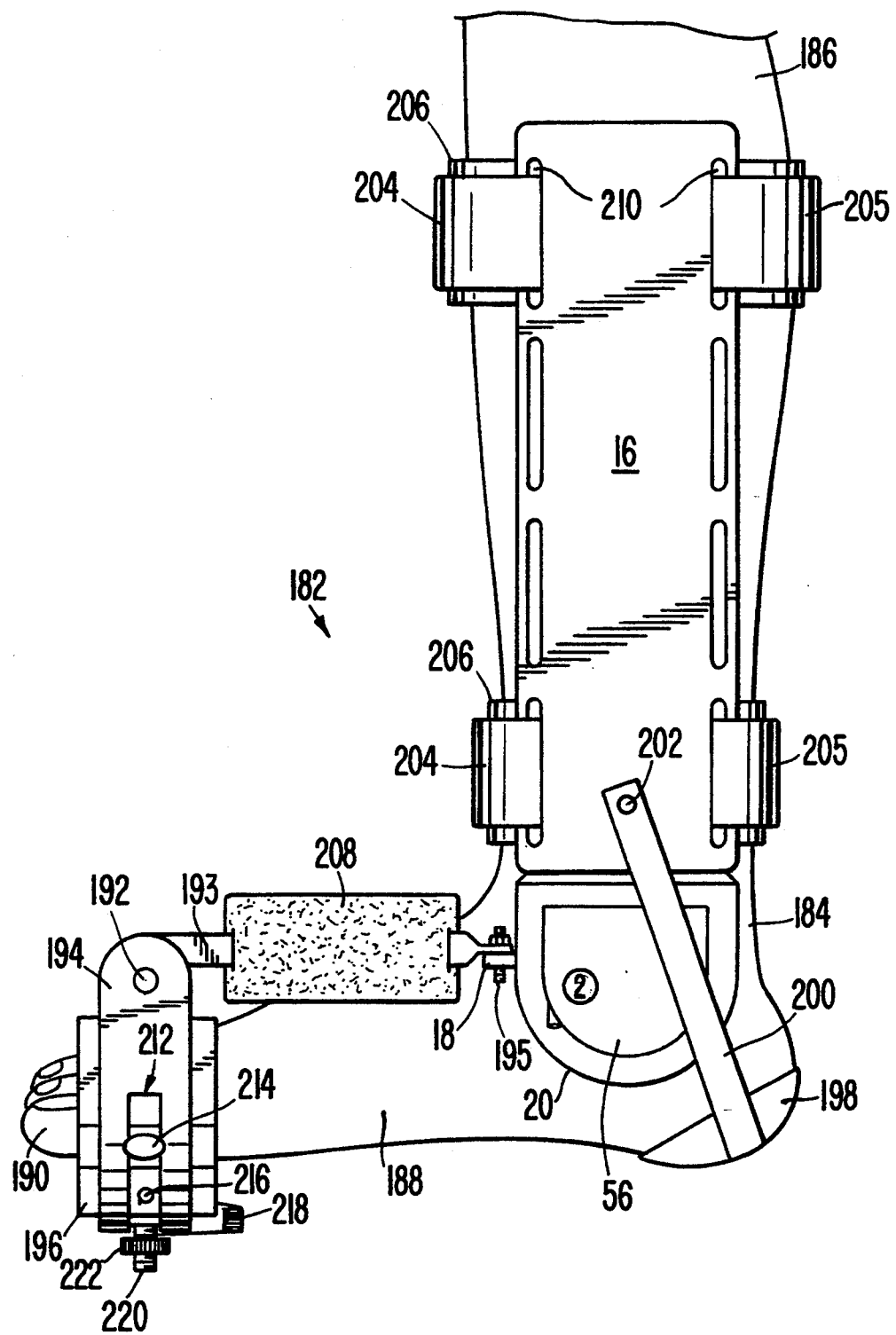
FIG. 14 is a side elevation of an ankle brace according to the present invention incorporating a novel foot pronation/supination cradle.

Referring now to FIGS. 1-5, the dynamic extension and/or flexion splint of the present invention indicated generally at 10 includes a suspension sleeve 12 formed from neoprene foam or similar material having some elasticity. The suspension sleeve is adapted to fit snugly around a limb or other body member in the area of a joint and operates to position a mechanical joint assembly 14 in alignment with a body joint. Suspension sleeve 12 provides a slight compression to the body member in the area of the affected body joint. This compression, and heat associated therewith, facilitates tissue nutrition which facilitates tissue growth.

A pair of mechanical joint assemblies 14 are mounted upon opposite sides of the suspension sleeve 12 as illustrated in FIG. 4, and each mechanical joint assembly includes first and second strut members 16 and 18 which extend outwardly from a mechanical joint or hinge structure 20. The strut members 16 and 18 are removably received in open ended, spaced pockets 22 and 24, respectively, and a pair of such pockets are secured to each of two opposite sides of the suspension sleeve 12. These pockets may be formed of leather or similar material, and operate to facilitate removal of a mechanical joint assembly 14 therefrom. When the mechanical joint assembly is in place within the pockets 22 and 24, the mechanical joint 20 will be retained in position at the side of a body joint to be treated. Adjustable posterior straps 26 and 28 and anterior straps 30 and 32 are secured to the pockets 22 and 24. The combination of an anterior and posterior strap is positioned on either side of the mechanical joint 20, and these straps cooperate to surround the limb of a user on either side of a joint to be treated. Such anterior and posterior straps insure that optimum therapeutic effectiveness is obtained from the spring tension provided by the mechanical joint 20.

The mechanical joint 20 is formed at ends of the strut members 16 and 18 which are pivoted about a pivot post 34. These pivoted ends of the strut members are bifurcated to provide an enclosure for an adjustable spring mechanism used to tension the mechanical joint 20. Thus, the first strut member 16 consists of a flat, elongate strut section 36 which, as it approaches the mechanical joint 20, is split into an upper leg 38 and a lower leg 40. The upper leg extends parallel to and is spaced from the lower leg by a bridging section 42.

Similarly, the second strut member 18 includes a flat, elongate strut section 44 having a bifurcated end with a lower leg 46 which extends parallel to but is spaced from an upper leg 48 by a bridging section 50. The upper and lower legs 38 and 40 and the upper and lower legs 46 and 48 are arcuate in configuration, as illustrated by the lower legs 40 and 46 shown in FIG. 5. The upper legs 38 and 48 substantially match the lower legs in configuration.

As illustrated in FIG. 3, the legs 46 and 48 fit within the legs 38 and 40, and are mounted for pivotal movement by the pivot post 34 which extends therethrough. This pivot post creates a pivotal axis which is substantially perpendicular to the longitudinal axes 52 and 54 of the strut sections 36 and 44, respectively.

A gear housing 56 is secured to the outermost surface of the upper leg 38, and operates to enclose a gear 58 mounted upon one end of the pivot post 34. This gear meshes with an adjustment screw 60 which is mounted for rotation in the gear housing 56. The adjustment screw has threads which engage the teeth of the gear 58 in known manner to rotate the gear and thereby rotate the pivot post 34. However, when the adjustment screw 60 is stationary, it locks the gear and the pivot post to the upper leg 38 and the lower leg 40. However, the lower leg 46 and upper leg 48 are mounted for pivotal movement about the pivot post 34.

As will be noted from FIG. 3, the pivot post extends completely through the upper legs 38 and 48 and the lower legs 40 and 46, and is held in place by a removable clip 62 which engages a groove in the pivot post. This removable clip may be formed by a spring clip, washer, or other known removable clip means, which can be removed from a groove in the pivot post 34 to facilitate disassembly of the mechanical joint 20. This permits a circular leaf-spring 64 to be mounted about the pivot post 34 between the lower and upper legs 46 and 48. One end 66 of this circular leaf-spring is secured within a central slot 68 formed in the pivot post 34, while an opposite end 70 of the leaf-spring is hooked about a post 72 which extends between the lower leg 46 and the upper leg 48. A second post 74 extends between the upper leg 38 and the lower leg 40, and this post is engaged by a step 76 formed in the periphery of the lower and upper legs 46 and 48 when the flat elongate strut sections 36 and 44 are in the extended position of FIG. 2.

The degree of tension set into the circular leaf-spring 64 may be indicated by indicia 132 on the gear 58 which cooperates with a stationary indicator 134 formed on the gear housing 56. Specifically, gear 58 may be marked about its periphery with a series of numbers or other markings indicating the relative tension existing on the spring when that marking occupies a defined position. Stationary indicator 134 may take the form of an aperture in gear housing 56 through which indicia 132 (i.e. the numbers or other markings) are visible.

As will be noted from FIG. 5, when the flat elongate strut sections 36 and 44 are pivoted toward one another in the direction of the arrows in FIG. 5, the steps 76 will move away from the post 74 and the pivotal movement will be opposed by the tension of the circular leaf-spring 64. Thus, the flat, elongate strut sections move from an extended position with the steps 76 in contact with the post 74 against the bias of the spring 64 to a second closed position wherein the first and second strut members come into contact and extend from the bottom side of the mechanical joint 20 in FIG. 5. As the flat elongate strut sections 36 and 44 are pivoted back to the extended position shown in FIG. 2, the pivotal movement is aided by the bias of the spring 64. It is obvious that this bias may be adjusted by rotating the adjustment screw 60 which in turn engages and rotates the gear 58 to rotate the pivot post 34. Depending upon the direction of rotation of the pivot post, the convolutions of the spring 64 will be tightened or loosened to adjust the bias of the spring.

It is noteworthy that the flat elongate strut sections 36 and 44 are formed from aluminum or similar lightweight, bendable material. Not only does this make the dynamic extension splint 10 light and compact, but it also permits the strut sections to be bent to conform to the outer contour of the limb of a user after the splint is in place to enhance comfort. Also, since the mechanical joint 20 can be disassembled by removing the spring clip 62, the spring 64 can be reversed to reverse the direction in which the spring aids or opposes pivotal movement. This facilitates therapeutic use of the dynamic extension splint 10 to provide either flexion or extension resistance.

Referring now to FIGS. 6 and 7, a second embodiment of the dynamic splint of the present invention is indicated generally at 78. For purposes of description, structural elements of dynamic splint 78 which are identical in structure and operation to those previously described in connection with dynamic splint 10 will be designated with like reference numerals. Also, in FIG. 6, only one side of dynamic splint 78 is illustrated, but it should be recognized that the first and second strut members and mechanical joint shown in FIG. 6 are provided on both sides of the suspension sleeve 12 as shown in FIG. 2.

Dynamic splint 78 includes a suspension sleeve 12 which differs from that of FIG. 1 in that it is provided with an opening 80 to receive the patella or another portion of a body joint to be treated. The sleeve also includes pull straps on either side connected to one end of the pocket 22. These pull straps, one of which is indicated at 82, are used to pull the sleeve 12 over a limb or a body member.

Dynamic splint 78 differs from dynamic splint 10 mainly in the structure of the mechanical joint, for the splint 78 includes a polycentric mechanical joint 84. This polycentric joint includes two spaced pivot pins 86 and 88 instead of the single pivot post 34 of FIG. 3. Each of these pivot pins extends through one of the bifurcated ends of the strut members 16 and 18. It will be noted that these bifurcated ends do not overlap, as illustrated in FIG. 3, but instead, are spaced apart by the pivot pins 86 and 88. Thus, as illustrated in FIG. 7, the first strut member 16 includes the flat elongate strut section 36, and a bridging section 90 which extends between a lower leg 92 and an upper leg 94. Similarly, the second strut member 18 includes the flat, elongate strut section 44 and a bridging section 96 which extends between a lower leg 98 and an upper leg 100. The bridging sections 90 and 96 space the lower legs 92 and 98 an equal distance from the upper legs 94 and 100, and circular leaf-springs 102 and 104 are mounted about the pivot pins 86 and 88 between the upper and lower legs of the first and second strut members. One end 106 of the spring 102 is hooked about a post 108 that extends between the lower leg 98 and the upper leg 100 of the second strut member 18, while an opposite end 110 of the spring 102 is secured within a slot 112 formed in the pivot pin 86. Similarly, one end 114 of the spring 104 is hooked about a post 116 which extends between the lower leg 92 and upper leg 94 of the first strut member 16, while a second end 118 of the spring is secured within a slot 120 formed in the pivot pin 88.

A housing 122 extends over the bifurcated ends of the first and second strut members 16 and 18 and encloses the polycentric mechanical joint 84. The pivot pins 86 and 88 extend outwardly on either side of the housing and on one side are clipped in place by the removable clips 62. The opposite ends of the pivot pins extend outwardly beyond the housing 122, and bear meshed gear members 124 and 126. These gear members operate to gear the pivot pins 86 and 88 together, and one gear member is mounted on the end of each of the pivot pins to rotate therewith. Secured to the end of each pivot pin and projecting above the respective gears 124 and 126 is a tool engaging adjustment knob, with two such adjustment knobs being indicated at 128 and 130. These adjustment knobs include a plurality of flat surfaces for engagement with a wrench-type tool that is used to turn the gears 124 and 126. For example, if the tool engages the adjustment knob 130 and turns the gear 126 in the direction of the arrow in FIG. 6, then both of the pivot pins 86 and 88 are turned by an equal amount due to the mesh between the gears 126 and 128. This adjusts the bias of the springs 102 and 104 an equal amount, and the degree of tension set into the springs may be indicated by indicia 132 on the gear 124 which cooperates with a stationary indicator 134 formed on the housing 122.

To lock the gears 124 and 126 in a desired position, a small locking gear 136 is provided on the end of an elongate slide member 138 which slides in a slot 140 formed in the housing 122. The locking gear 136 has teeth which engage the teeth of the gears 124 and 126 to lock these gears in place. To unlock these gears for purposes of bias adjustment, the slide member 138 is moved to the left in FIG. 6 to disengage the gear 136. The slide member may be manipulated by means of a knob 142 provided on the end thereof opposite to the locking gear 136.

The housing 122 is formed with indentations 144 and 146 to engage the first and second strut members 16 and 18. These indentations provide stops for the strut members in the extended position shown in FIG. 6. However, the two strut members may be moved together to the left in FIG. 6 for a full 180° due to the polycentric construction of the mechanical joint 84. As the strut members pivot, the pivotal movement is transmitted by the posts 108 and 116 to the springs 102 and 104, and these springs oppose pivotal movement between an extended and a closed position in one direction while aiding pivotal movement in the opposite direction. The bias of the two springs may be adjusted equally by rotating one of the gears 124 or 126 to accomplish rotation of the opposite gear for an equal amount and therefore rotation of the pivot pins 86 and 88.

As in the case of the spring 64, the springs 102 and 104 can be reversed by removing the clips 62 and disassembling the mechanical joint 84. Thus the dynamic extension splint 78 can be configured to provide either flexion or extension resistance.

The dynamic extension splints 10 and 78 may be provided with an adjustable range of motion stop assembly to limit the degree of motion a body member is permitted to make around a body joint. For many types of injuries, it is beneficial to rehabilitate the body joint in stages with the degree of motion permitted by the splints being increased as free motion in a previous stage is achieved. With reference to FIGS. 8-10, the mechanical joint 14 for the dynamic extension splint 10 includes an arcuate line of spaced holes 150 and 152 formed in the legs 38 and 40 respectively. A hole 150 is aligned with a corresponding hole 152 to receive one of the spring biased pins 154 or 156 extending from opposite ends of a stop 158. The stop 158 includes a stop housing 160 that retains the pins 154 and 156 which are biased outwardly from the ends of the stop housing by a spring 162. The stop housing extends across the legs 46 and 48 so that when the pins extend into selected holes 150 and 152, the stop 158 will engage the legs 46 and 48 to limit the relative pivotal movement of the struts 16 and 18. To remove or adjust the position of the stop 158, the pins 154 and 156 are compressed into the stop housing 160 so that the stop can be disengaged from the holes 150 and 152.

The dynamic extension splint 78 shown in FIGS. 11 and 12 is also provided with a range of motion stop assembly including a plurality of arcuately arranged spaced holes 164 and 166 formed in the upper and lower edges respectively of the housing 122. As shown in FIG. 12, which is a view of a portion of the mechanical joint 84 with the springs 102 and 104 removed for purposes of illustration, two stops 158 are positioned to span the distance between the upper and lower edges of the housing 122, with a stop extending in front of each of the bifurcated ends of the strut members 16 and 18. The spring biased pins 154 and 156 for each stop extend into a hole 164 and 166 respectively in the housing 122. Thus, each stop limits the range of pivotal movement of a strut member 16 or 18 depending upon where the stop is positioned in the line of holes 164 or 166.

FIG. 13 is an exploded view of a preferred embodiment of the mechanical joint 20 which provides a locking means for relieving the action of the bias mechanism during installation and removal of dynamic extension splint 10. In this embodiment, mechanical joint 20 has a hole 170 through housing 56 of mechanical joint 20. A hole 172 of size and shape similar to that of hole 170 is formed in strut member 18, which rotates relative to housing 56 and strut member 16 as explained previously. Holes 170 and 172 are formed at the same distance from the axis of rotation of strut member 18 (i.e. pivot post 34, not shown) so that holes 170 and 172 are aligned, at one point in the rotation of strut member 18 relative to housing 56, along a locking pin insertion axis 174 parallel to the axis of rotation of strut member 18. At the point of alignment of holes 170 and 172, locking pin 176 can be inserted through both holes 170 and 172 to prevent relative motion of strut members 16 and 18. Locking pin 176 comprises knob 178 and elongated pin 180. Of course, a plurality of holes 170 or holes 172 could also be provided to provide several points of alignment at which strut members 16 and 18 could be locked together. Also, holes 170 and 172 and locking pin 176 can be provided on either one or both of the two mechanical joints 20 of a given dynamic extension splint 10, as desired.

In use, locking pin 176, together with holes 170 and 172, can be used to remove the bias force provided by mechanical joint 20 during attachment and removal of dynamic extension splint 10 from the affected body part. The elimination of the bias force during attachment and removal simplifies the attachment and removal process, particularly when larger bias forces are being applied. Specifically, any bias force components tending to act against the forces needed to disengage components of dynamic extension splint 10 from the affected body part will be neutralized. This neutralization of bias forces also prevents any springing back of strut members 16 or 18 when one of strut members 16 or 18 is released from the affected body part and the other is still attached. Such springing action as a result of bias forces during removal of the device could aggravate the injuries being treated with dynamic extension splint 10, or cause further injuries. Of course, bias force could also be reduced by adjusting the tension on mechanical joints 20. However, the use of locking pin 176 permits complete elimination of the bias force without disturbing the desired bias force setting.

Referring now to FIG. 14, an ankle splint according to the present invention is shown generally at 182, attached to a human ankle 184 connecting leg 186 to foot 188 having toes 190. Ankle splint 182 comprises two strut members 16, one on each side of leg 186, which are rotatably connected via mechanical joints 20 (which is of a type described previously) to struts 18, one on each side. Struts 18 are rotatably connected by fasteners 195 to arms 193 which are rotatably connected by pins 192 to a central cradle 194 which supports a foot carriage 196. Foot carriage 196 is connected to travel in an arc relative to cradle 194 along slot 212. Fasteners 214 loosely connect foot carriage 196 to cradle 194 to permit this arc-like movement. Fasteners 214 are preferably of nylon or incorporate nylon bearing washers to facilitate sliding of carriage 196 along slot 212. A spring 218 is mounted between attachment 216 (mounted on carriage 196) and a tensioning bolt 220 mounted through slot 212 and held in position along slot 212 by nut 222.

Fasteners 195 can be loosened to laterally adjust the angle of arms 193 to compensate for deviations in alignment of the foot. Fasteners 195 will then be tightened to hold arms 193 firmly to struts 18.

Struts 16 are attached to leg 186 by extension straps 204 and flexion straps 205 which pass through opposite holes 210 at the front and back respectively of one of the two struts 16, and are then attached to similar straps 204 and 205 associated in the same manner with the strut 16 on the other side of leg 186. The attachment of straps 204 and 205 is preferably by hook-and-loop fasteners, such as Velcro, although other types of strap connecting hardware could also be used. Optionally, a heel cup 198 may be provided for further stabilizing ankle splint 182 with respect to ankle 184. A strap 200 connects heel cup 198 to ankle splint 182 via a snap 202 or other appropriate fastening means. Cuffs 206 are installed on leg 186 under straps 204 to prevent chafing and increase comfort during use. Cuffs 206 are made from a three-part laminate comprising a central layer of split neoprene, an outer layer of loop material for use with hook-and-loop fasteners, and an inner non-allergenic padding and lining layer. Cuffs 206 have loop fastener material section 207 attached to the inner layer of cuffs 206 at an edge 211 thereof parallel to the longitudinal axes of struts 16. Cuffs 206 will be provided in an oversize circumference, and may then be cut at the end opposite from edge 211 bearing loop fastener material section 207, to fit the particular patient's body part. Loop fastener material section 207 will engage the outer layer of cuffs 206 at any point about cuffs 206, thus providing a continuously-adjustable snug fit around leg 186. Strut 18 may be provided with a pad 208 of sheepskin or other soft material. Struts 16 are of aluminum or other relatively soft metal to facilitate bending of struts 16 by the installer to conform to the shape of leg 186.

Figure 15:
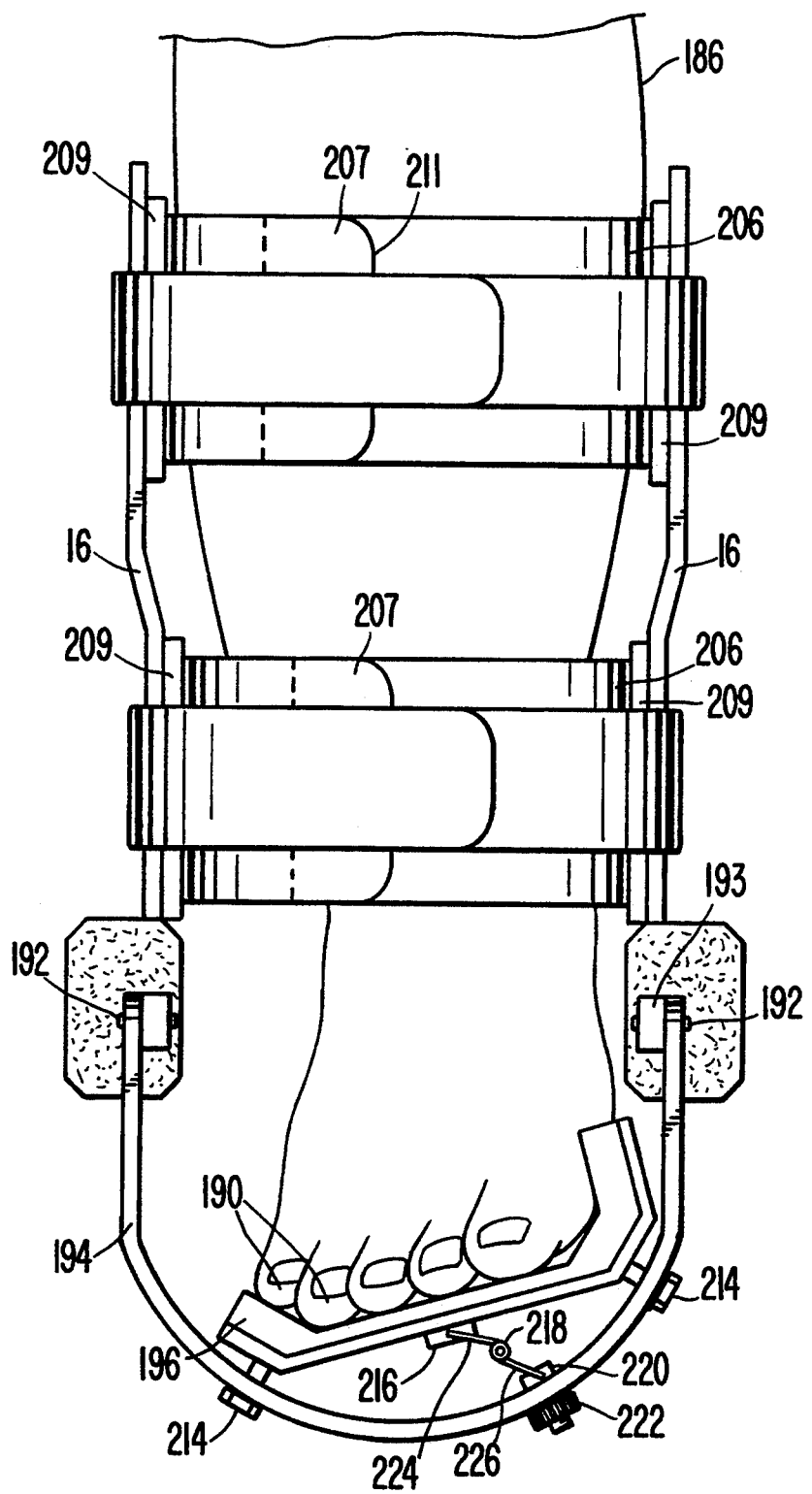
FIG. 15 is a front elevation of the ankle brace of FIG. 14.

FIG. 15, which is a frontal view of ankle splint 182, shows more clearly the bending of strut 16 to conform strut 16 to the shape of leg 186. As a further attachment means, struts 16 have hook fastener material 209 attached to their inner surfaces, and hook fastener material 209 engages the loop fastener material on the outer layers of cuffs 206 to hold struts 16 in position with respect to cuffs 206. Carriage 196 receives the ball of foot 188. Of course, the configuration of cuffs 206 can be changed depending on the application. Either a plurality of smaller cuffs 206 or one larger cuff 206 can be provided in the mounting area of ankle splint 182.

Ankle splint 182, through the bias force provided by mechanical joints 20, provides therapy for correction of both plantar flexion and dorsiflexion limitations. As will be seen, the bias force provided by spring 218 acting on carriage 196 also permits correction of inversion and eversion of the foot. Since inversion or eversion accompany a large percentage of ankle abnormalities, ankle splint 182 provides a major advance in total dynamic therapy for the lower leg, ankle, and foot.

Referring now to FIG. 15, it will be seen that spring 218 is of the type having two arms 224 and 226 extending outwardly from a central biasing device, such as a wire coil, which provides a force biasing arms 224 and 226 toward a rest position in which arms 224 and 226 are separated. Arm 224 is connected to attachment 216 of carriage 196, and arm 226 is connected to tensioning bolt 220. The arms 224 and 226 may pass through holes provided in attachment 216 and tensioning bolt 220, or may be attached in some other appropriate way. Depending on the positioning of tensioning bolt 220 anywhere along slot 212, spring 218 provides a variable biasing force tending to move carriage 196 in one or the other direction along slot 212. As carriage 196 moves along slot 212, it rotates in an arc relative to ankle 184, tending to rotate the end of foot 188 in the region of toes 190 relative to ankle 184. Also, due to the shape of cradle 194, the ball of the foot 188 tends to move up or down relative to ankle 184 as it rotates under the influence of spring 218. Thus, cradle 194, carriage 196, spring 218, and their associated components, in conjunction with the other components of ankle splint 182, comprise a means for applying a bias force tending to rotate foot 188 laterally relative to ankle 184, while at the same time applying a bias force tending to move the end of foot 188 up or down relative to ankle 184. The cradle 194 is designed to be reversible in its connection to arms 193 to accommodate both left and right feet.

Figure 16:
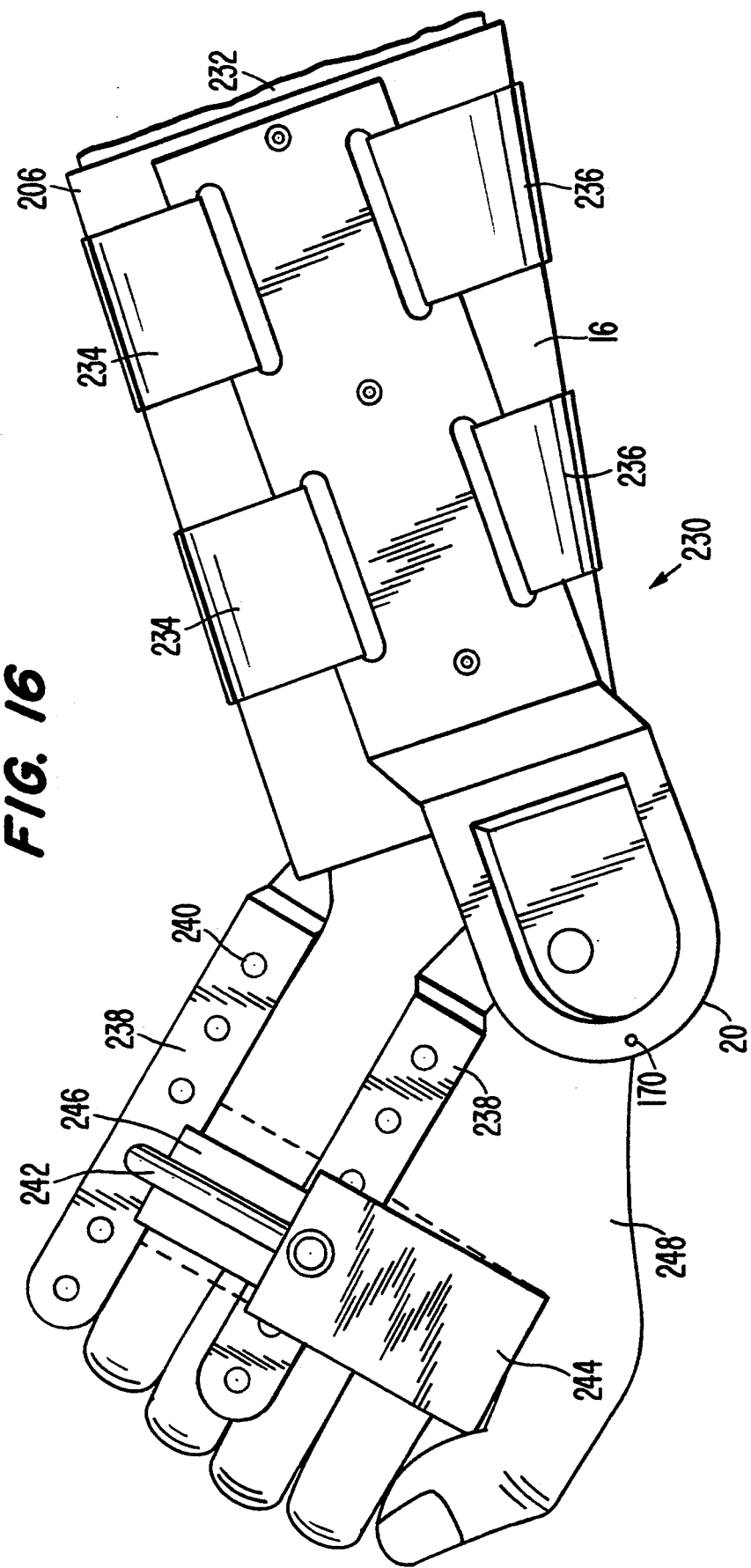
FIG. 16 is a side view of a wrist brace according to the present invention incorporating a novel palm interface structure.

FIG. 16 shows a wrist splint 230 designed according to the invention. An elastic neoprene cuff 206 similar to the cuffs 206 described previously is attached about forearm 232, and flexion straps 234 and extension straps 236 are attached about cuff 206, using hook-and-loop fastener material or other adjustable attaching methods, to connect two struts 16 located on the sides of forearm 232. Each strut 16 is fixed to a mechanical joint 20. Struts 238 are attached to mechanical joint 20 to rotate relative thereto and to be biased in one direction or the other depending on the assembly of mechanical joint 20, as described previously. Each strut 238 has a series of adjustment holes 240 spaced along its length. Depending on the size of the patient's hand 248, axial pin 242 will be installed through and between two corresponding adjustment holes 240, one on each strut 238. Axial pin 242 is a structural member which connects struts 238 to hold struts 238 parallel. Axial pin 242 also provides an attaching point for a palm strap 244, and defines an axis about which palm strap 244 rotates. Strap member 246 is attached to axial pin 242 or palm strap 244 across the back of hand 248. In this embodiment, straps 244 and 246 are preferably made of fairly rigid material, such as thin aluminum. In actual use, straps 244 and 246 will be padded for comfort with sheepskin or other appropriate padding material as described previously with respect to other embodiments. However, to avoid obscuring structural parts in the drawing, this padding material is not shown in FIG. 16.

In use, palm strap 244 transmits the bias force of mechanical joints 20, where appropriate, to oppose extension of the wrist. Significantly, the distance between palm strap 244 and mechanical joint 20 is adjustable by installation of axial pin 242 in different pairs of adjustment holes 240. Also, palm strap 244 rotates about axial pin 242 during extension of the wrist, so that palm strap 244 maintains its location relative to the palm of hand 248. This rotating action is important, since the distance between the palm and mechanical joints 20 will vary during movement of the hand about the axis extending between mechanical joints 20. The rotating motion of palm strap 244 provides a means for dynamically adjusting the location of palm strap 244 in the palm in response to changes in the orientation of hand 248.

Strap 246 transmits the bias force of mechanical joints 20 to oppose flexion of the wrist when mechanical joints 20 are adjusted to provide a flexion-opposing bias force.

FIG. 17 is a top view of the wrist splint 230 of FIG. 16 showing a dorsal support 250 mounted along the dorsal side of forearm 232 and held in place by flexion straps 234. The rounded end of dorsal support 250 is placed immediately to the side of the styloid process, toward the center of the wrist. Preferably, dorsal support 250 has hook fastener material mounted on its underside to connect with the loop fastener material on the exterior of cuff 206, thus further holding dorsal support 250 in place relative to the wrist. Dorsal support 250 is of aluminum or other bendable rigid material. Dorsal support 250 provides additional rigidity and support for the attachment of wrist splint 230 to forearm 232 when wrist splint 230 is applied to oppose extension of the wrist. In particular, during extension of the wrist, the dorsal support 250 delivers the counterforce of the wrist splint 230 to the wrist axis at an optimal point. Dorsal support 250 will not be used when wrist splint 230 is configured to oppose flexion of the wrist.

FIG. 18 shows a preferred embodiment of a wrist splint generally at 251. The attachment of wrist splint 251 to forearm 232 is substantially similar to that previously described with reference to FIGS. 16 and 17 for wrist splint 230, and will not be repeated here. Wrist splint 251 differs from wrist splint 230 in that relatively short strut members 252 are attached to mechanical joints 20 to rotate relative thereto, biased by the bias force exerted by mechanical joint 20 as described previously. Elongated rigid arms 254 are attached to each of the struts 252 through one end of arms 254 by fasteners 256. Fasteners 256 may be hex head screws, and are chosen so that they may be loosened, permitting arms 254 to rotate about the axis defined by the length of fasteners 256, and then tightened to hold arms 254 at a desired angle with respect to struts 252.

The ends of arms 254 not attached to struts 252 are attached through slots 255 to opposite ends of an elongated rigid crossbar 258 through slot 259 by additional fasteners 256 which, as described above, can be loosened to permit adjustment of the angles between arms 254 and crossbar 258, and tightened to hold arms 254 and crossbar 258 relatively immobile. A palm strap 260 is attached at opposite ends to opposite ends of crossbar 258 to rotate about an axis parallel to the central longitudinal axis of crossbar 258. The adjustments provided by slots 255 and 259 permit adjustment of the length of the moment arm from the wrist axis to the palmar crease to suit the individual patient. In addition, the angular adjustability of the structure shown allows compensation for radial and ulnar deviation.

FIG. 19 is a bottom view of wrist splint 251 of FIG. 18 and shows the palm interface of wrist splint 251 in greater detail. Palm strap 260 is a flexible strap, which may be made from heavy nylon fabric and provided with metal fasteners or snaps for rotatable attachment to crossbar 258. A palm pad 262, shaped to fit the palm with a cutout region to accomodate the thumb, is attached to palm strap 260. Palm pad 262 is preferably made of a fairly rigid yet flexible material, such as urethane. Palm strap 260 and palm pad 262 may be reinforced with thin aluminum inserts to provide added rigidity and structural strength. The aluminum inserts can be bent to provide a uniform loading across the concave surface of the transverse arch. Palm strap 260, palm pad 262, and crossbar 258 will generally be covered with lambs wool or other padding material (not shown) when wrist splint 251 is in use.

In use, the wrist splint 251 shown in FIGS. 18 and 19 can be adjusted to compensate for differences in angle between hand 248 and forearm 232 by adjusting the relative angles of struts 252, arms 254, and crossbar 258 before tightening fasteners 256. As an additional comfort feature, palm pad 262 provides a means for distributing the bias force provided by mechanical joints 20 over a larger area of the palm. The flexible characteristics of palm strap 260 and palm pad 262 combine with the rotation of palm strap 260 relative to crossbar 258 to provide a dynamically self-adjusting force distribution apparatus throughout the range of motion of hand 248.

It is a particular feature of all of the designs discussed and shown previously that the split cuffs and straps are not located on the joint itself. Thus, counterforces are never applied directly to the joint. In many cases, the affected joint will have been injured and may be painful or swollen. Thus, this feature permits use of the dynamic splint of the present invention even during the early recovery stages of an injury to the affected joint.

As noted previously, the mechanical joints in the dynamic splints of the present invention preferably allow full range of motion of the affected joint, plus 10% in either direction. This design provides a substantial advantage in that the joint is not immobilized during use of the splints, and everyday activities can be performed if necessary while wearing the splints. Full movement of the affected body parts during wearing of the splints enhances blood flow and thus tissue health. In addition, a full range of motion prevents stiffness in the direction other than that being treated. Thus, the dynamic splints of the present invention will not create a flexion limitation by limiting motion in the flexion direction during treatment of an extension problem.

INDUSTRIAL APPLICABILITY

The dynamic splint of the present invention is used for the treatment of joint contractures occurring secondary to trauma, casting, or other immobilization. It is also used to restore strength and flexibility to a body joint, by creating resistance requiring the wearer to flex the joint, thereby building strength and fluidity. The bias adjustment feature incorporated within the dynamic extension splint permits the spring bias of the splint to be varied throughout a recovery process as treatment of the Joint progresses.

The dynamic splints disclosed permit maintenance of a defined tolerable force level with near constant linearity over a wide range of motion of a body joint. The dynamic splints are particularly useful for prophylactic maintenance of range-of-motion and mobility, particular in post-operative cases.

We claim:

1. An adjustable splint device for applying force across a body joint comprising a first strut member having a longitudinal axis extending between opposed ends thereof, a second strut member having a longitudinal axis extending between opposed ends thereof, joint means for connecting one end of said first and second strut members for pivotal movement bout a pivot axis which is transverse to the longitudinal axes of said first and second strut members, said joint means including pivot means for mounting at least one of said first and second strut members for pivotal movement about said pivot means, bias means connected to provide a bias to oppose pivotal movement of said first and second elongated strut members in a first direction and to aid such pivotal movement in a second direction opposite to said first direction, said bias means being connected to said pivot means and to at least one of said first and second strut members, bias adjustment means mounted at said joint means and operative to rotate said pivot means to adjust the bias of said bias means, and locking means for selectively preventing any relative movement of said first and second strut members.

2. The device of claim 1 wherein the locking means comprises a pin insertable through a hole in said first strut member and a hole in another portion of the device which rotates about said pivot means relative to said first strut member, such that said insertion of the pin prevents said rotation.

3. The device of claim 1 wherein the locking means includes at least a first hole in said first strut member, at least a second hole in said second strut member and a pin insertable through said first hole into said second hole to prevent relative movement of said first and second strut members.

4. The device of claim 3 wherein said first hole is formed to align with said second hole at a position along an arc of pivotal movement of at least one of said first or second strut members about said pivot means, insertion of said pin in said first and second holes operating to lock said first strut member to said second strut member to neutralize the bias of said bias means to aid in the attachment or removal of said splint device across a body joint.

5. The device of claim 4 wherein said first and second strut members each include a bifurcated end section having first and second spaced legs, said joint means connecting the bifurcated end section of said first strut member to the bifurcated end section of said second strut member for relative pivotal movement.

6. The device of claim 5 wherein the first and second legs respectively of the bifurcated end section of said first strut member are connected adjacent to the first and second legs respectively of the bifurcated end section of said second strut member, said first hole being formed nit he first leg of the bifurcated end section of said first strut member and said second hole being formed in the first leg of the bifurcated end section of said second strut member, said bias adjustment means including gear means connected to said pivot means to cause rotation thereof to adjust the bias of said bias means, said gear means being mounted between the first and second legs of the bifurcated end sections of said first and second strut members.

7. The device of claim 6 wherein said bias adjustment means includes a rotatable shaft having gear teeth thereon mounted to engage said gear means to rotate said gear means upon the rotation of said rotatable shaft.

8. The device of claim 7 wherein spaced indicia are provided on the gear means to indicate the degree of bias provided by said bias means at different positions of said gear means.

9. The device of claim 8 wherein at least one viewing opening is provided in the first leg of at least one of the bifurcated end sections of said first and second strut members to expose said indicia, said spaced indicia being arranged to pass sequentially under said viewing opening as said gear means is rotated.

10. The device of claim 9 wherein the locking means includes at least a first hole in said first strut member, at least a second hole in said second strut member and a pin insertable through said first hold into said second hole to prevent relative movement of said first and second strut members.

11. An adjustable splint device for applying force across a body joint comprising a first strut member having a longitudinal axis extending between opposed ends thereof, a second strut member having a longitudinal axis extending between opposed ends thereof, joint means for connecting one end of said first and second strut members for pivotal movement about a pivot axis which is transverse to the longitudinal axes of said first and second strut members, said joint means including pivot means for mounting at least one of said first and second strut members for pivotal movement about said pivot means, bias means connected to provide a bias to oppose pivotal movement of said first and second elongated strut members in a first direction and to aid such pivotal movement in a second direction oppose to said first direction, said bias means being connected to said pivot means and to at least one of said first and second strut members, bias adjustment means mounted at said joint means and operative to rotate said pivot means relative to the strut member to which said bias means is attached to adjust the bias of said bias means, and force indicating means mounted at said joint means for providing a visible indication of the magnitude of said bias, said force indicating means including an indicia bearing member mounted to rotate with said pivot means.

12. The device of claim 11 wherein said joint means is enclosed in a housing, and said force indicating means comprises a series of markings on said member rotated with said pivot means, at least one of said markings being visible through said housing.

13. The device of claim 12 wherein said markings are numerals.

14. The device of claim 12 wherein the housing is provided with an aperture through which only a limited portion of the markings on said rotated member is visible, whereby the visible limited portion of markings provides the indication of bias magnitude.

15. The device of claim 12 wherein said bias means comprises a spring disposed about the pivot means, and said rotated means, the rotation of said rotated member causing variation of tension on said spring.

16. A multiaxial splint device for applying forces across a body joint connecting first and second body members, comprising:
a first elongated strut member on each of opposing sides of the first body member having a longitudinal axis extending between opposed first and second ends thereof;
a second elongated strut member on each of said opposing sides of second body member having a longitudinal axis extending between opposed first and second ends thereof;
joint means for connecting the first ends of said first and second strut members on each side of the first and second body members for pivotal movement about a pivot axis transverse to the longitudinal axes of said first and second strut members, said joint means including pivot means for mounting at least one of said first and second strut members for pivotal movement about said pivot means;
bias means connected to said first and second elongated strut members on each side of the first and second body members to provide first bias forces to oppose pivotal movement of said first and second elongated strut members in a first direction and to aid such pivotal movement in a second direction opposite to said first direction;
torsion means attached to both first elongated strut members for providing a second, torsional bias force on said first body member aiding rotation of the joint in a first torsional direction about an axis substantially perpendicular to said pivot axis, and opposing rotation of the joint in a second torsional direction opposite to said first torsional direction.

17. The splint device of claim 16 wherein said torsion means comprises variable bias means or varying the magnitude of said torsional bias force.

18. The splint device of claim 16 wherein said said first body member is a foot, said second body member is a leg, and said joint is an ankle connecting said foot and leg.

19. A multiaxial splint device for applying forces across a body connecting first and second body members, comprising:
a first elongated strut member on each of opposing sides of the first body member having a longitudinal axis extending between opposed first and second ends thereof;
joint means for connecting the first ends of said first and second strut members on each side of the first and second body members for pivotal movement about a pivot axis transverse to the longitudinal axes of said first and second strut members, said joint means including pivot means for mounting at least one of said first and second strut members for pivotal movement about said pivot means;
bias means connected to said first and second elongated strut members on each side of the first and second body members to provide first bias forces to oppose pivotal movement of said first and second elongated strut members in a first direction and to aid such pivotal movement in a second direction opposite to said first direction;
torsion means attached to both first elongated strut members for providing a second torsional bias force on said first body member aiding rotation of the joint in a first torsional direction about an axis substantially perpendicular to said pivot axis, and opposing rotation of the joint in a second torsional direction opposite to said first torsional direction, said torsion means comprising a cradle defining a path of movement for said first body member, and a carriage receiving said first body member and movable along said movement path of the cradle.

20. The splint device of claim 19 wherein the cradle includes an elongated slot, the carriage includes guide means for engaging said slot, and said slot receives said guide portion to guide the carriage along said movement path.

21. The splint device of claim 19 wherein the cradle defines an arcuate movement path.

22. The splint device of claim 21 wherein the cradle includes an elongated arcuate slot, the carriage includes guide means for engaging said slot, and said slot receives said guide portion to guide the carriage along said movement path.

23. The splint device of claim 22 further comprising spring means for aiding movement of the carriage in a first direction along said arcuate slot and opposing movement of the carriage in a second direction opposite the first.

24. The splint device of claim 23 wherein the spring means comprises a spring having two elongated arms connected by a biasing coil biasing the arms toward a defined separated position, one arm of said spring being connected to the carriage at a first location and one being connected to the cradle at a second location.

25. The splint device of claim 24 wherein at least one of the first and second locations are adjustable in the direction of elongation of the slot to provide a variable bias.

26. An adjustable splint device for applying force across a body joint comprising a first strut member, a second strut member, said first and second strut members each including a bifurcated end section having first and second spaced legs, joint means for connecting the bifurcated end section of said first strut member to the bifurcated end section of said second strut member for relative pivotal movement about a pivot axis, said joint means including pivot means for mounting at least one of said first and second strut members for pivotal movement about said pivot means, said bifurcated end sections of said first and second strut members being connected together by said pivot means to form a central receiving space at said joint means through which said pivot means extends, bias means connected to provide a bias to oppose pivotal movement of said first and second strut members in a first direction and to aid such pivotal movement in a second direction opposite to said first direction, said bias means being connected to at least one of said first and second strut members, bias adjustment means mounted at said joint means and operative to adjust the bias of said bias means, a force indicating means mounted for rotation in said central receiving space for providing a visible indication of the magnitude of the bias of said bias means, said bias adjustment means operating to rotate said force indicating means during operation of said bias adjustment means to adjust said bias, and locking means formed at said joint means for selectively preventing all relative movement of said first and second elongated strut members.

27. The device of claim 26 wherein the locking means includes at least a first hole in said first strut member, at least a second hole in said second strut member and a pin insertable through said first hole into said second hole to prevent relative movement of said first and second strut members.

28. The device of claim 27 wherein said first hole is formed to align with said second hole at a position along an arc of pivotal movement of at least one of said first or second strut members about said pivot means, insertion of said pin in said first and second holes operating to lock said first strut member to said second strut member to neutralize the bias of said bias means to aid in the attachment or removal of said splint device across a body joint.

29. The device of claim 26 wherein said pivot means is mounted for rotation by asid bias adjustment means, said force indicating means being mounted on said pivot means.

30. The device of claim 29 wherein said bias means is connected to said pivot means, the bias of said bias means being varied by rotation of said pivot means.

31. The device of claim 30 wherein the first and second legs respectively of the bifurcated end section of said first strut member are connected adjacent to the first and second legs respectively of the bifurcated end section of said second strut member, said first hole being formed in the first leg of the bifurcated end section of said first strut member and said second hole being formed in the first leg of the bifurcated end section of said second strut member, said bias adjustment means including gear means connected to said pivot means to cause rotation thereof to adjust the bias of said bias means, said gear means being mounted between the first and second legs of the bifurcated end sections of said first and second strut members.

32. The device of claim 31 wherein said bias adjustment means includes a rotatable shaft having gear teeth thereon mounted to engage said gear means to rotate said gear means upon the rotation of said rotatable shaft.

33. The device of claim 32 wherein said spaced indicia are provided on the gear means to indicate the degree of bias provided by said bias means at different positions of said gear means.

34. The device of claim 33 wherein at least one viewing opening is provided in the first leg of at least one of the bifurcated end sections of said first and second strut members to expose said indicia, said spaced indicia being arranged to pass sequentially under said viewing opening as said gear is rotated.

* * * * *